United States Patent
Prabhakara et al.

(10) Patent No.: US 12,097,183 B2
(45) Date of Patent: *Sep. 24, 2024

(54) PHARMACEUTICAL COMPOSITION FOR TREATING MIGRAINE

(71) Applicant: TONIX MEDICINES, INC., Chatham, NJ (US)

(72) Inventors: Prabhu Prabhakara, Udupi (IN); Rajesh Ramesh Patil, Thane (IN); Piyush Gupta, Ghaziabad (IN); Rajeev Singh Raghuvanshi, Gurgaon (IN); Anil N. Namboodiripad, Yardley, PA (US)

(73) Assignee: Tonix Medicines, Inc., Chatham, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/833,105

(22) Filed: Jun. 6, 2022

(65) Prior Publication Data

US 2022/0387386 A1    Dec. 8, 2022

Related U.S. Application Data

(63) Continuation of application No. 16/718,414, filed on Dec. 18, 2019, now Pat. No. 11,364,224, which is a continuation of application No. 15/011,357, filed on Jan. 29, 2016, now Pat. No. 10,537,554.

(30) Foreign Application Priority Data

Aug. 5, 2015    (IN) ............................ 4076/CHE/2015

(51) Int. Cl.
*A61K 31/4045*    (2006.01)
*A61K 9/00*    (2006.01)
*A61K 9/08*    (2006.01)

(52) U.S. Cl.
CPC ........ *A61K 31/4045* (2013.01); *A61K 9/0019* (2013.01); *A61K 9/08* (2013.01)

(58) Field of Classification Search
None
See application file for complete search history.

(56) References Cited

U.S. PATENT DOCUMENTS

| | | |
|---|---|---|
| 4,816,470 A | 3/1989 | Dowle et al. |
| 10,537,554 B2 | 1/2020 | Prabhakara |
| 11,364,224 B2 | 6/2022 | Prabhakara et al. |

OTHER PUBLICATIONS

Freitag, F.G. "Sumatriptan needle-free subcutaneous (Sumavel) approved for the acute treatment of migraine, with or without aura, and cluster headaches," Exper. Rev. Neurother., vol. 11, No. 4, pp. 481-491 (2011).

Rothrock et al. "A review of needle-free sumatriptan injection for rapid control of migraine," Headache, vol. 53 (suppl. 2), pp. 21-23 (Sep. 2013).

Afshinmajd, S. et al. "The effects of body mass index on the treatment of the patients with migraine headaches," Iranian Journal of Neurology, 10(3-4): 35-38 (2011).

Alsuma (Alsuma Label) Prescribing Information, Jun. 2010, Distributed by US WorldMeds, pp. 1-32.

Anonymous: "Imitrex (sumatriptan succinate) Injection", Jan. 2006 (Jan. 2006 ), pp. 1-25, XP055267215, Internet Retrieved from the internet: URL:http://www.accessdata.fda.gov/drugsatfda_docs/label/2006/020080s036lbl.pdf [retrieved on Apr. 20, 2016].

Anonymous: "Sumavel DosePro (sumatriptan injection), for subcutaneous use", Jan. 2014 (Jan. 2014 ), pp. 1-8, XP055267185, internet. Retrieved from the Internet: URL:http://www.sumaveldosepro.com/pdf/pi.pdf [retrieved on Apr. 20, 2016].

Berteau, C., et al. "Evaluation of the impact of viscosity, injection volume, and injection flow rate on subcutaneous Injection tolerance," Medical Devices: Evidence and Research, 8: 473-484 (2015).

Brazeau, G.A. et al. "Current perspectives on pain upon injection of drugs," J. Pharm. Sci 87(6): 667-677 (Jun. 1998). Abstract Only.

Brazeau, G.A. et al., "Current Perspective on Pain upon Injection of Drugs," Jun. 1998, Journal of Pharmaceutical Sciences, 87(6):667-77.

Burke-Ramirez, P. et al. "Efficacy and tolerability of subcutaneous sumatriptan for acute migraine: a comparison between ethnic groups." Headache, 41(9): 873-882 (Oct. 2001).

Cady et al., "An Open-Label, Pilot Study of DFN-11 Injection (Sumatriptan 3 mg) for Medication Overuse Headache," 3 pages.

Cady, "Clinvest Research Study Report: Randomized, Double-Blind, Crossover, Comparator Pilot Study of DFN-11 Injection (Sumatriptan 3mg versus 2X3 mg [6mg] for Rapidly Escalating Migraine," May 19, 2016, 17 pages.

GlaxoSmithKline (Imitrex® Package Insert NDA 20-080/S-036, dated Jan. 2006).

Gregor, N et al.: "Treatment of cluster headache attacks with less than 6 mg subcutaneous sumatriptan", Headache, vol. 45, No. 8, Sep. 2005 (Sep. 2005), pp. 1069-1072, XP002756962.

Holmberg, Monica. "Zembrace SymTouch," Pharmacy Times (2016). Website (www.zembrace.com—accessed Jan. 18, 2017).

Interface Analysis Associates, Migraine Autoinjector Comparison Study Report—AI Comparison Study of Zembrace SymTouch, Imitrex STATdose, and Sumavel DosePro Autoinjector Devices, May 9, 2016, 214 pages.

Lamon-Fava, S. et al. "Impact of Body Mass Index on Coronary Heart Disease Risk Factors in Men and Women," Arteriosclerosis, Thrombosis and Vase Biol 16(12): 31 pgs (1996).

Landy, S. et al., "An Open-Label Trial of a Sumatriptan Auto-Injector for Migraine in Patients Currently Treated With Subcutaneous Sumatriptan*" 2013, Headache, 53:118-25.

(Continued)

*Primary Examiner* — Craig D Ricci

(74) *Attorney, Agent, or Firm* — HALEY GUILIANO LLP; James F. Haley, Jr.; Stacey W. Chung

(57) ABSTRACT

The present application relates to a method of treating migraine or cluster headache in a human patient, said method comprising administering subcutaneously composition comprising sumatriptan or its pharmaceutically acceptable salt, in an amount equivalent to 3 mg sumatriptan base.

6 Claims, No Drawings

(56) References Cited

OTHER PUBLICATIONS

Landy, S. et al. "An Open-Label Trial of a Sumatriptan Auto-Injector for Migraine in Patients Currently Treated With Subcutaneous Sumatriptan," Headache, 53(1): 118-125 (2012). Abstract Only.

Landy, S., et al.: "Pilot study evaluating preference for 3-mg versus 6-mg subcutaneous sumatriptan", Headache, vol. 45, No. 4, Apr. 2005 (Apr. 2005), pp. 346-349, XP002756961.

Landy, Stephen, et al. "Efficacy and safety of DFN-11 (sumatriptan injection, 3 mg) in adults with episodic migraine: a multicenter, randomized, double-blind, placebo-controlled study," The Journal of Headache and Pain (2018), 19:69 (9 pages).

Landy, Stephen, et al. "Efficacy and safety of DFN-11 (sumatriptan injection, 3 mg) in adults with episodic migraine: an 8-week open-label extension study," The Journal of Headache and Pain (2018), 19:70 (8 pages).

Mauskop, "Injectable sumatriptan: Imitrex, Sumavel, Alsuma," Sep. 6, 2012, New York Headache blog, 2 pages.

PCT International Search Report and Written Opinion for International Application No. PCT/US2016/015961 issued on May 9, 2016.

Smith, "Clinvest Research Study Report: DFN-11-CD-007: Open Label, Efficacy and Safety Pilot Study of DFN-11 Injection (Sumatriptan 3mg) in Medication Overuse Headache," Dec. 2, 2016, 22 pages.

Taylor, F. "Weight Change Associated with the Use of Migraine-Preventive Medications," Clinical Therapeutics, 30 (6): 1069-1080 (Nov. 2008).

Visser, W. H. et al.: "Sumatriptan-nonresponders: a survey in 366 migraine patients", Headache, vol. 36, No. 8, Sep. 1996 (Sep. 1996), pp. 471-475, XP002756963.

Visser, W. H. et al.: "Treatment of migraine attacks with subcutaneous sumatriptan: first placebo-controlled study. The Subcutaneous Sumatriptan International Study Group", Cephalalgia: An International Journal of Headache, vol. 12, No. 5, Oct. 1992 (Oct. 1992), pp. 308-313, XP009189707.

Watanabe, Y. et al. "Monitoring cortical hemodynamic changes after sumatriptan injection during migraine attack by hear-infrared spectroscopy," Neuroscience Research, Elsevier, Shannon, Ireland, 69(1): 60-66 (Jan. 1, 2011).

Zembrace (Zembrace SymTouch Label) Prescribing Information, Section 6, Adverse Reactions. Revised Jun. 2019, 3 pages.

Zembrace SymTouch Prescribing Information (revised Jan. 2016).

Zembrace SymTouch Website (www.zembrace.com—accessed Jan. 18, 2017).

PHARMACEUTICAL COMPOSITION FOR TREATING MIGRAINE

PRIORITY

This application is a continuation application of U.S. patent application Ser. No. 16/718,414, filed Dec. 18, 2019, which is a continuation application of U.S. patent application Ser. No. 15/011,357, filed Jan. 29, 2016, issued as U.S. Pat. No. 10,537,554 on Jan. 21, 2020, which claims priority to Indian Patent Application No. 4076/CHE/2015 filed Aug. 5, 2015, the entire disclosures of each of which are incorporated herein by reference in their entireties. A certified copy of Indian Application No. 4076/CHE/2015 was provided in and is available in U.S. patent application Ser. No. 15/011,357.

BACKGROUND

Field

The present disclosure relates to compositions and methods for treating migraine or cluster headache in a human patient.

Description of the Related Art

Migraine is a common neurological disorder that greatly affects quality of life and increases work disruption. An average of 6% and 17% of men and women, respectively, suffer from migraine headache. The cause of migraine is uncertain but may be the result of vascular and/or neurological dysfunction.

Sumatriptan has been approved for treatment of migraines and is available in various dosage forms, such as subcutaneous injection, oral tablets and nasal spray and marketed in different strengths (6 to 100 mg). Sumatriptan is a serotonin type 1 receptor agonist that has a selective but heterogeneous effect on the carotid arterial system to relieve migraines. Current theories proposed to explain the etiology of migraine headache suggest that symptoms are due to local cranial vasodilatation and/or to the release of sensory neuropeptides (including substance P and calcitonin gene-related peptide) through nerve endings in the trigeminal system. The therapeutic activity of sumatriptan for the treatment of migraine is thought to be due to the agonist effects at the 5-HT 1B/1D receptors on intracranial blood vessels (including the arterio-venous anastomoses) and sensory nerves of the trigeminal system, which result in cranial vessel constriction and inhibition of pro-inflammatory neuropeptide release (IMITREX® Injection Labeling, October 2012).

The approved IMITREX® subcutaneous injection products for the acute treatment of migraine, with or without aura, are available in 4 mg/0.5 mL and 6 mg/0.5 mL concentrations as single-dose pre-filled syringes (PFSs) for use with an autoinjector pen (IMITREX® STATdose, NDA 020080), and as a single-dose vial of 6 mg/0.5 mL for SC injection (IMITREX®).

These available subcutaneous injections of sumatriptan products have moderate to severe side effects. To lower the incidence of side effects and to increase the patient adherence to sumatriptan therapy there is always a need for newer strength of sumatriptan subcutaneous injection product.

SUMMARY

Some embodiments disclosed herein provide methods of treating migraine or cluster headache in a patient in need thereof, said method comprising: subcutaneously administering to the patient a composition comprising an aqueous solution of sumatriptan or its pharmaceutically acceptable salts thereof in an amount equivalent to 3 mg of sumatriptan base, and sodium chloride in an amount to maintain the osmolality of said solution between 275 to 315 mOsm/kg; wherein said sumatriptan and sodium chloride are present in a ratio of from about 0.80:1.00 to about 1.40:1.00; wherein said composition has a pH of about 4.2 to 5.3; and wherein the subcutaneous administration of said composition to the patient results in a systemic exposure characterized by at least one of the following plasma profiles: (a) $C_{max}$ of about 35 ng/ml to about 57 ng/ml; (b) $AUC_{0-2}$ of about 30 ng·hr/ml to about 50 ng·hr/ml; (c) $AUC_{0-inf}$ of about 43 ng·hr/ml to about 70 ng·hr/ml.

In some embodiments, the methods comprise measuring the patient's body mass index (BMI). In some embodiments, the subcutaneous administration results in a systemic exposure that is greater in patients with a BMI of less than about 26 compared to patients with a BMI of greater than or equal to about 26. In some embodiments, the subcutaneous administration results in a systemic exposure that is greater than that achieved by an equivalent dose of a commercially available sumatriptan in patients with a BMI of less than about 26. In some embodiments, the equivalent dose (3 mg) of the commercially available sumatriptan is half of a 6 mg sumatriptan subcutaneous injection sold under the brand name of IMITREX®. In some embodiments, the subcutaneous administration results in a systemic exposure that is higher in white patients than in non-white patients. In some embodiments, the subcutaneous administration results in a $C_{max}$ that is greater than 50 ng/ml in patients having a BMI of less than about 26. In some embodiments, the subcutaneous administration results in an $AUC_{0-2}$ that is greater than 40 ng·hr/ml in patients having a BMI of less than about 26. In some embodiments, the subcutaneous administration results in an $AUC_{0-inf}$ that is greater than 60 ng·hr/ml in patients having a BMI of less than about 26.

Some embodiments disclosed herein provide methods of treating migraine or cluster headache in a patient in need thereof, said method comprising: measuring the BMI of the patient; selecting the patient having a BMI of less than about 26; subcutaneously administering to the patient a composition comprising an aqueous solution of sumatriptan or its pharmaceutically acceptable salts thereof in an amount equivalent to 3 mg of sumatriptan base, and sodium chloride in an amount to maintain the osmolality of said solution between 275 to 315 mOsm/kg; wherein said sumatriptan and sodium chloride are present in a ratio of from about 0.80:1.00 to about 1.40:1.00; wherein said composition has a pH of about 4.2 to 5.3; and wherein the subcutaneous administration of said composition to the patient results in a systemic exposure characterized by at least one of the following plasma profiles: (a) $C_{max}$ of about 35 ng/ml to about 57 ng/ml; (b) $AUC_{0-2}$ of about 30 ng·hr/ml to about 50 ng·hr/ml; (c) $AUC_{0-inf}$ of about 43 ng·hr/ml to about 70 ng·hr/ml.

In some embodiments, the subcutaneous administration results in a systemic exposure that is greater than that achieved by an equivalent dose of a commercially available sumatriptan. In some embodiments, the equivalent dose (3 mg) of the commercially available sumatriptan is half of a 6 mg sumatriptan subcutaneous injection sold under the brand name of IMITREX®.

Some embodiments disclosed herein provide methods of treating migraine or cluster headache in a patient, said method comprising: subcutaneously administering to the patient, at a maximum recommended frequency according to the body mass index (BMI) of the patient, a composition comprising an aqueous solution of sumatriptan or its pharmaceutically acceptable salts thereof in an amount equivalent to 3 mg of sumatriptan base, and sodium chloride in an amount to maintain the osmolality of said solution between 275 to 315 mOsm/kg; wherein said sumatriptan and sodium chloride are present in a ratio of from about 0.80:1.00 to about 1.40:1.00; wherein said composition has a pH of about 4.2 to 5.3; and wherein the subcutaneous administration of said composition to the patient results in a systemic exposure characterized by at least one of the following plasma profiles: (a) $C_{max}$ of about 35 ng/ml to about 57 ng/ml; (b) $AUC_{0-2}$ of about 30 ng·hr/ml to about 50 ng·hr/ml; (c) $AUC_{0-inf}$ of about 43 ng·hr/ml to about 70 ng·hr/ml.

In some embodiments, the maximum recommended frequency of administration is not more than four times a day if the BMI is less than about 26. In some embodiments, the maximum recommended frequency of administration is not more than four times a day if the BMI is greater than or equal to about 26.

DETAILED DESCRIPTION

Definitions

Unless otherwise defined, all technical and scientific terms used herein have the same meaning as commonly understood by one of ordinary skill in the art.

The term "about," as used herein, means within 10% of a given value or range. Alternatively, the term "about" means within an acceptable standard error of the mean.

The term "sumatriptan" herein refers to sumatriptan or its pharmaceutically acceptable salt. The amount of sumatriptan pharmaceutically acceptable salt used in the composition as per this disclosure is equivalent to 3 mg of sumatriptan base. For example 4.2 mg of sumatriptan succinate salt is equivalent to 3 mg of sumatriptan base.

The term "migraine" herein refers to migraine with or without aura.

The term "treating migraine" herein refers to acute treatment of migraine attacks with or without aura.

The term "treating cluster headache" herein refers to acute treatment of cluster headache episodes, with or without migraine.

A therapeutic agent or a protective agent may comprise a "drug." As used herein, a "drug" refers to a therapeutic agent or a diagnostic agent and includes any substance, other than food, used in the prevention, diagnosis, alleviation, treatment, or cure of a disease. Stedman's Medical Dictionary, 25th Edition (1990). The drug can include any substance disclosed in at least one of: The Merck Index, 12th Edition (1996); Pei-Show Juo, Concise Dictionary of Biomedicine and Molecular Biology, (1996); U.S. Pharmacopeia Dictionary, 2000 Edition; and Physician's Desk Reference, 2001 Edition. In some embodiments, the therapeutic agent is one of the embodiments of the compositions described herein.

The term "comprising" as used herein is synonymous with "including," "containing," or "characterized by," and is inclusive or open-ended and does not exclude additional, unrecited elements or method steps.

Other objects, advantages and features of the present disclosure will become apparent from the following specification.

Sumatriptan Compositions

Some embodiments disclosed herein provide sumatriptan compositions comprising an aqueous solution of sumatriptan or its pharmaceutically acceptable salts thereof in an amount equivalent to 3 mg of sumatriptan base and sodium chloride in an amount to maintain the osmolality of said solution between 275 to 315 mOsm/kg. In some embodiments, the sumatriptan and sodium chloride are present in a ratio of from about 0.80:1.00 to about 1.40:1.00. In some embodiments, the sumatriptan compositions have a pH of 4.2 to 5.3.

In some embodiments, the compositions comprise an aqueous solution of sumatriptan or its pharmaceutically acceptable salts thereof in an amount equivalent to 3 mg of sumatriptan base and sodium chloride in an amount to maintain the osmolality of said solution between 275 to 315 mOsm/kg; wherein said sumatriptan and sodium chloride are present in a ratio of from about 0.80:1.00 to about 1.40:1.00, and wherein the total volume of the sumatriptan compositions is about 0.5 ml.

In some embodiments, the compositions comprise an aqueous solution of sumatriptan or its pharmaceutically acceptable salts thereof in an amount equivalent to 3 mg of sumatriptan base and sodium chloride in an amount to maintain the osmolality of said solution between 275 to 315 mOsm/kg; wherein said sumatriptan and sodium chloride are present in a ratio of from about 0.80:1.00 to about 1.40:1.00, wherein the sumatriptan compositions have a pH of 4.2 to 5.3, and wherein the total volume of the sumatriptan compositions is about 0.5 ml.

In some embodiments, the compositions comprise an aqueous solution of sumatriptan or its pharmaceutically acceptable salts thereof in an amount equivalent to 3 mg of sumatriptan base and sodium chloride in an amount to maintain the osmolality of said solution between 275 to 315 mOsm/kg; wherein said sumatriptan and sodium chloride are present in a ratio of from about 0.80:1.00 to about 1.40:1.00, and wherein the sumatriptan compositions have a pH of 4.2 to 5.3 and are stable for the period of at least 3 months when stored at 40±2° C. and 75±5% relative humidity.

In some embodiments, the compositions comprise about 0.5 ml of aqueous solution of sumatriptan or its pharmaceutically acceptable salts thereof in an amount equivalent to 3 mg of sumatriptan base and sodium chloride in an amount to maintain the osmolality of said solution between 275 to 315 mOsm/kg; wherein said sumatriptan and sodium chloride are present in a ratio of from about 0.80:1.00 to about 1.40:1.00, and wherein the sumatriptan compositions have a pH of 4.2 to 5.3 and are stable for the period of at least 3 months when stored at 40±2° C. and 75±5% relative humidity.

In some embodiments, the compositions comprise an aqueous solution of sumatriptan or its pharmaceutically acceptable salts thereof in an amount equivalent to 3 mg of sumatriptan base and sodium chloride in an amount to maintain the osmolality of said solution between 275 to 315 mOsm/kg; wherein said sumatriptan and sodium chloride are present in a ratio of from about 0.80:1.00 to about 1.40:1.00, and wherein the sumatriptan compositions have a pH of 4.2 to 5.3 and are stable for the period of at least 12 months when stored at 30±2° C. and 65±5% relative humidity.

In some embodiments, the compositions comprise about 0.5 ml of aqueous solution of sumatriptan or its pharmaceutically acceptable salts thereof in an amount equivalent to 3 mg of sumatriptan base and sodium chloride in an amount to maintain the osmolality of said solution between 275 to 315 mOsm/kg; wherein said sumatriptan and sodium chloride are present in a ratio of from about 0.80:1.00 to about 1.40:1.00, and wherein the sumatriptan compositions have a pH of 4.2 to 5.3 and are stable for the period of at least 12 months when stored at 30±2° C. and 65±5% relative humidity.

In some embodiments, the compositions comprise an aqueous solution of sumatriptan or its pharmaceutically acceptable salts thereof in an amount equivalent to 3 mg of sumatriptan base and sodium chloride in an amount to maintain the osmolality of said solution between 275 to 315 mOsm/kg; wherein said sumatriptan and sodium chloride are present in a ratio of from about 0.80:1.00 to about 1.40:1.00, and wherein the sumatriptan compositions have a pH of 4.2 to 5.3 and are stable for at least 3 months at 40° C./75% relative humidity or for at least 12 months at 30° C./65% relative humidity.

In some embodiments, the compositions comprise about 0.5 ml of aqueous solution of sumatriptan or its pharmaceutically acceptable salts thereof in an amount equivalent to 3 mg of sumatriptan base and sodium chloride in an amount to maintain the osmolality of said solution between 275 to 315 mOsm/kg; wherein said sumatriptan and sodium chloride are present in a ratio of from about 0.80:1.00 to about 1.40:1.00, and wherein the sumatriptan compositions have a pH of 4.2 to 5.3 and are stable for at least 3 months at 40° C./75% relative humidity or for at least 12 months at 30° C./65% relative humidity.

The sumatriptan solution may be formulated in a variety of compositions, for example, as a sterile injectable composition. A sterile injectable composition, such as a sterile injectable aqueous or oleaginous suspension, may be formulated according to techniques known in the art using suitable dispersing or wetting agents and suspending agents. The sterile injectable preparation may also be a sterile injectable solution or suspension in a non-toxic parenterally acceptable diluent or solvent. Among the acceptable vehicles and solvents that may be employed include mannitol, water, Ringer's solution and isotonic sodium chloride solution. Suitable carriers and other pharmaceutical composition components are typically sterile.

Methods of Treating Migraine or Cluster Headache

Some embodiments disclosed herein provide methods of treating migraine or cluster headache in a patient in need thereof, said method comprising: subcutaneously administering to the patient a composition comprising an aqueous solution of sumatriptan or its pharmaceutically acceptable salts thereof in an amount equivalent to 3 mg of sumatriptan base, and sodium chloride in an amount to maintain the osmolality of said solution between 275 to 315 mOsm/kg.

To practice the methods disclosed herein, the sumatriptan composition may be adjusted to have a pH that is suitable for subcutaneous administration, such as a pH of about 4.2 to 5.3. The aqueous solution of sumatriptan or its pharmaceutically acceptable salts thereof and sodium chloride may be present in the composition in any suitable ratios, for example, from about 0.80:1.00 to about 1.40:1.00.

Commercially available sumatriptan subcutaneous injection could be 6 mg sumatriptan subcutaneous injection sold under the brand name of IMITREX® by GlaxoSmithKline or its generic versions. Commercially available sumatriptan subcutaneous injection may also include 4 mg sumatriptan subcutaneous injection sold under the brand name of IMITREX® STATdose by GlaxoSmithKline or its generic versions.

The subcutaneous administration of the sumatriptan composition as disclosed herein may result in a systemic exposure that is equivalent to or greater than that achieved by an equivalent dose (3 mg) of a commercially available sumatriptan in patients, e.g., half of a 6 mg sumatriptan subcutaneous injection sold under the brand name of IMITREX®. For example, the subcutaneous administration of the sumatriptan composition as disclosed herein may result in a systemic exposure, e.g., $C_{max}$, $AUC_{0-t}$, $AUC_{0-2}$ or $AUC_{0-inf}$ that is equivalent to or greater than that achieved by an equivalent dose of a commercially available sumatriptan in patients. In some embodiments, the subcutaneous administration of the sumatriptan composition as disclosed herein may result in a systemic exposure, e.g., $AUC_{0-2}$, $AUC_{0-t}$, $AUC_{0-2}$ or $AUC_{0-inf}$ that is higher than that achieved by an equivalent dose of a commercially available sumatriptan in patients. In some embodiments, the subcutaneous administration of the sumatriptan composition as disclosed herein may result in a systemic exposure, e.g., $C_{max}$, $AUC_{0-t}$, $AUC_{0-2}$ or $AUC_{0-inf}$ that is about the same of that achieved by a higher dose, e.g., 4 mg, of a commercially available sumatriptan in patients.

In some embodiments, a method of treating migraine or cluster headache in a patient in need thereof is disclosed. The method includes subcutaneously administering to the patient a composition comprising an aqueous solution of sumatriptan or its pharmaceutically acceptable salts thereof in an amount equivalent to 3 mg of sumatriptan base, and sodium chloride in an amount to maintain the osmolality of the solution between 275 to 315 mOsm/kg. The sumatriptan and sodium chloride are present in a ratio of from about 0.80:1.00 to about 1.40:1.00. The composition has a pH of about 4.2 to 5.3. Subcutaneous administration of the composition to the patient results in a systemic exposure characterized by at least one of the following plasma profiles: $C_{max}$ of about 35 ng/ml to about 57 ng/ml; $AUC_0$-2 of about 30 ng·hr/ml to about 50 ng·hr/ml; $AUC_{0-t}$ of about 41 ng·hr/ml to about 68 ng·hr/ml; and $AUC_{0-inf}$ of about 43 ng·hr/ml to about 70 ng·hr/ml.

In some embodiments, the subcutaneous administration of said composition to the patient results in a systemic exposure that is at 90% Confidence Interval (CI) of the relative mean of $C_{max}$, $AUC_{0-t}$, $AUC_{0-inf}$ and $AUC_{0-2}$ within 80.00% to 125.00% of 0.25 ml of commercially available 6 mg/0.5 ml sumatriptan subcutaneous injection.

In some embodiments, the subcutaneous administration of the sumatriptan composition may result in a systemic exposure that is significantly higher in certain patients than in other patients. For example, in some embodiments, the subcutaneous administration results in a systemic exposure that is significantly higher in white patients than in non-white patients.

Effects of Body Mass Index (BMI) on Systemic Exposure

Without being bound by theory, the presently disclosed methods result in systemic exposures that correlate to the BMI of the patients being treated. For example, the subcutaneous administration of the sumatriptan composition results in a systemic exposure that is greater in patients with a lower BMI compared to patients with a higher BMI. In some embodiments, the subcutaneous administration results in a systemic exposure that is greater in patients with a BMI of less than about 26 compared to patients with a BMI of greater than or equal to about 26. The difference between the systemic exposure of patients with a BMI of less than about 26 and a systemic exposure of patients with a BMI of greater than or equal to about 26 may be statistically significant.

Therefore, in some embodiments, the methods disclosed herein may comprise measuring the patient's BMI. The BMI is defined as the body mass divided by the square of the body height, and is universally expressed in units of $kg/m^2$, resulting from mass in kilograms and height in meters.

It will be appreciated that the correlation between the systemic exposure and the BMI of the patient may be used in a variety of ways to optimize the effectiveness and/or minimize the side effects of the sumatriptan composition disclosed herein. For example, the BMI of the patients may be used to select patients that will achieve a higher systemic exposure, and therefore more effectiveness using the sumatriptan composition disclosed herein. The BMI of the patients may also be used to select patients that will achieve similar effectiveness using the 3 mg sumatriptan composition disclosed herein as using the higher dose, e.g., 4 mg or 6 mg, of a commercially available sumatriptan, and therefore fewer side effects. Alternatively, the BMI of the patients may be used to calculate the maximum recommended frequency of administration of the sumatriptan composition disclosed herein. In some embodiments, patients with a higher BMI will be given a higher maximum recommended frequency of administration in comparison to patients with a lower BMI.

Patient Selection

Accordingly, some embodiments disclosed herein provide methods of treating migraine or cluster headache in a patient in need thereof, said method comprising: measuring the BMI of the patient; selecting the patient having a BMI of less than about 26; subcutaneously administering to the patient a composition comprising an aqueous solution of sumatriptan or its pharmaceutically acceptable salts thereof in an amount equivalent to 3 mg of sumatriptan base, and sodium chloride in an amount to maintain the osmolality of said solution between 275 to 315 mOsm/kg.

The subcutaneous administration of the sumatriptan composition as disclosed herein may result in a systemic exposure that is equivalent to or greater than that achieved by an equivalent dose (3 mg) of a commercially available sumatriptan, e.g., half of a 6 mg sumatriptan subcutaneous injection sold under the brand name of IMITREX®, in patients with a BMI of less than about 26. For example, the subcutaneous administration of the sumatriptan composition as disclosed herein may result in a systemic exposure, e.g., $C_{max}$, $AUC_{0-t}$, $AUC_{0-2}$ or $AUC_{0-inf}$, that is equivalent to or greater than that achieved by an equivalent dose of a commercially available sumatriptan, e.g., half of a 6 mg sumatriptan subcutaneous injection sold under the brand name of IMITREX®, in patients with a BMI of less than about 26. In some embodiments, the subcutaneous administration of the sumatriptan composition as disclosed herein may result in a systemic exposure, e.g., $C_{max}$, $AUC_{0-t}$, $AUC_{0-2}$ or $AUC_{0-inf}$ that is higher than that achieved by an equivalent dose of a commercially available sumatriptan, e.g., half of a 6 mg sumatriptan subcutaneous injection sold under the brand name of IMITREX®, in patients with a BMI of less than about 26. In some embodiments, the subcutaneous administration of the sumatriptan composition as disclosed herein may result in a systemic exposure in patients with a BMI of less than about 26, e.g., $C_{max}$, $AUC_{0-t}$, $AUC_{0-2}$ or $AUC_{0-inf}$ that is about the same of that achieved by a higher dose, e.g., 4 mg or 6 mg, of a commercially available sumatriptan in patients with a BMI of greater than or equal to about 26.

Some embodiments disclosed herein provide methods of treating migraine or cluster headache in a patient in need thereof, said method comprising: measuring the BMI of the patient; selecting the patient having a BMI of greater than or equal to about 26; subcutaneously administering to the patient a composition comprising an aqueous solution of sumatriptan or its pharmaceutically acceptable salts thereof in an amount equivalent to 3 mg of sumatriptan base, and sodium chloride in an amount to maintain the osmolality of said solution between 275 to 315 mOsm/kg.

The subcutaneous administration of the sumatriptan composition as disclosed herein may result in a systemic exposure that is equivalent to or greater than that achieved by an equivalent dose (3 mg) of a commercially available sumatriptan, e.g., half of a 6 mg sumatriptan subcutaneous injection sold under the brand name of IMITREX®, in patients with a BMI of greater than or equal to about 26. For example, the subcutaneous administration of the sumatriptan composition as disclosed herein may result in a systemic exposure, e.g., $C_{max}$, $AUC_{0-t}$, $AUC_{0-2}$ or $AUC_{0-inf}$ that is equivalent to or greater than that achieved by an equivalent dose of a commercially available sumatriptan, e.g., half of a 6 mg sumatriptan subcutaneous injection sold under the brand name of IMITREX®, in patients with a BMI of greater than or equal to about 26. In some embodiments, the subcutaneous administration of the sumatriptan composition as disclosed herein may result in a systemic exposure, e.g., $C_{max}$, $AUC_{0-t}$, $AUC_{0-2}$ or $AUC_{0-inf}$ that is higher than that achieved by an equivalent dose of a commercially available sumatriptan, e.g., half of a 6 mg sumatriptan subcutaneous injection sold under the brand name of IMITREX®, in patients with a BMI of greater than or equal to about 26.

Methods of Reducing Side Effects

Some embodiments disclosed herein provide methods of treating migraine or cluster headache in a patient in need thereof, said method comprising: subcutaneously administering to the patient a composition comprising an aqueous solution of sumatriptan or its pharmaceutically acceptable salts thereof in an amount equivalent to 3 mg of sumatriptan base, and sodium chloride in an amount to maintain the osmolality of said solution between 275 to 315 mOsm/kg; wherein incidences of side effects are reduced at least 10% compared with commercially available sumatriptan subcutaneous injection.

The generally observed adverse or side effects of sumatriptan can be categorized as atypical sensations which includes tingling, warm or hot sensation, feeling of heaviness, burning sensation, numbness, feeling strange, tight feeling in head; cardiovascular adverse effect such as which includes discomfort in throat, nasal cavity/sinuses, flushing, chest discomfort, tightness in chest, pressure in chest, ear, nose, and throat; musculoskeletal adverse effect such as weakness, Neck pain/stiffness myalgia; neurological adverse effect such as dizziness or vertigo, drowsiness or sedation; miscellaneous adverse effects such as jaw discomfort and sweating.

It would be appreciated that the incidence of side effects may be directly or indirectly associated with the systemic exposure in a patient. Therefore, to reduce the incidence of side effects, it may be desirable to lower the systemic exposure in comparison to a commercially available sumatriptan. For example, the methods disclosed herein may result in a lower systemic exposure in patients in comparison to patients treated with a higher dose, e.g., 4 mg or 6 mg, of a commercially available sumatriptan. In some embodiments, the methods disclosed herein may result in a systemic exposure that is 10%, 20%, 30%, 40%, 50% lower in patients in comparison to patients treated with a higher dose, e.g., 4 mg or 6 mg, of a commercially available sumatriptan.

The methods disclosed herein may also be used to reduce the incidence of side effects by lowering the systemic exposure in patients with low or high BMI in comparison to patients treated with a commercially available sumatriptan. In some embodiments, the methods disclosed herein may result in a systemic exposure that is 10%, 20%, 30%, 40%, 50% lower in patients with a BMI of less than about 26 in comparison to patients with a BMI of less than about 26 treated with a higher dose, e.g., 4 mg or 6 mg, of a commercially available sumatriptan. In some embodiments, the methods disclosed herein may result in a systemic exposure that is 10%, 20%, 30%, 40%, 50% lower in patients with a BMI of greater than or equal to about 26 in comparison to patients treated with a higher dose, e.g., 4 mg or 6 mg, of a commercially available sumatriptan with a BMI of greater than or equal to about 26. In some embodiments, the methods disclosed herein may result in a systemic exposure that is 10%, 20%, 30%, 40%, 50% lower in patients with a BMI of greater than or equal to about 26 in comparison to patients treated with a higher dose, e.g., 4 mg or 6 mg, of a commercially available sumatriptan with a BMI of less than about 26. In some embodiments, the methods disclosed herein may result in a systemic exposure that is 10%, 20%, 30%, 40%, 50% lower in patients with a BMI of less than about 26 in comparison to patients treated with a higher dose, e.g., 4 mg or 6 mg, of a commercially available sumatriptan with a BMI of greater than or equal to about 26.

Methods of Adjusting Frequency of Administration

Some embodiments disclosed herein provide methods of treating migraine or cluster headache in a patient in need thereof, said method comprising: subcutaneously administering to the patient, at a maximum recommended frequency according to the body mass index (BMI) of the patient, a composition comprising an aqueous solution of sumatriptan or its pharmaceutically acceptable salts thereof in an amount equivalent to 3 mg of sumatriptan base, and sodium chloride in an amount to maintain the osmolality of said solution between 275 to 315 mOsm/kg. In some embodiments, the maximum recommended frequency of administration is not more than four times a day if the BMI is less than about 26. In some embodiments, the maximum recommended frequency of administration is not more than four times a day if the BMI is greater than or equal to about 26.

Methods for Treating Medication Overuse Headache or Rapid Escalating Migraine

Some embodiments disclosed herein provide methods for treating medication overuse headache or rapid escalating migraine in a patient in need thereof, said method comprnsmg: subcutaneously administering subcutaneously administering a composition comprising an aqueous solution of sumatriptan or its pharmaceutically acceptable salts thereof in an amount equivalent to 3 mg of sumatriptan base, and sodium chloride in an amount to maintain the osmolality of said solution between 275 to 315 mOsm/kg.

In some aspects of the above embodiments, the methods do not require detoxification of patients including withdrawal of the overused drugs.

Methods of Making the Sumatriptan Compositions

Some embodiments disclosed herein provide methods of making a composition comprising an aqueous solution of present application is manufactured by a two-step process comprising the steps of:

mixing sodium chloride m 80% (of batch size) of water for injection and preparing a solution; and adding required quantity of sumatriptan or its pharmaceutically acceptable salts thereof in the solution of step a, and making the final volume up to 100% (of batch size) using water for injection; wherein the process steps being performed in said order to maintain the osmolality of said solution between 275 to 315 mOsm/kg and increases solubility of sumatriptan by at least 9 percent.

In some embodiments, the composition disclosed herein may be sterilized by filtration. Terminal sterilization may cause instability and increase in impurities in the compositions disclosed herein.

In some embodiments, the compositions disclosed herein may be manufactured in light controlled conditions. U.V. and visible light may cause instability and increase in impurities in the compositions disclosed herein.

In some embodiments, the compositions disclosed herein can be dispensed by suitable device such autoinjector devices, prefilled syringes, ampoules, vials, a glass vial, a plastic vial etc.

In some embodiments, the compositions disclosed herein can be dispensed by pre-filled syringe fully assembled into an auto-injector device.

In some embodiments, the compositions disclosed herein can be dispensed in disposable, single-use auto-injector containing about 0.5 mL of sumatriptan succinate in an amount equivalent to 3.0 mg of sumatriptan base in a pre-filled syringe (PFS) fully assembled for ready use.

In some embodiments, the compositions disclosed herein can be dispensed in suitable devices that are suitable for containment and administration. Further, the devices are packed in suitable secondary package a material that envelops the devices. The secondary packaging provides additional barriers to elements that can degrade the composition such as light and oxygen. Some devices may also be designed to permeable to oxygen and other gases. For example, syringes, cartridges and the like can have permeable parts to allow sterilization process with, for example, ethylene oxide.

In some embodiments, the compositions disclosed herein compnse a secondary packaging in addition to the dispensed devices. Secondary packaging includes any container that receives the device (e.g., a box, bag, blister, canister, bottle and the like) and is sealed to prevent ingress of oxygen. The secondary packaging is made from material that has very low permeability to oxygen molecules (e.g., ethylene vinyl alcohol, aluminum, glass, polyamide and the like). In certain instances, the secondary packaging further comprises an oxygen absorber inside. The oxygen absorber functions to absorb any oxygen present in the secondary packaging. Suitable materials for oxygen absorbers include iron, low molecular weight organic compounds such as ascorbic acid and sodium ascorbate and polymeric materials incorporating a resin and a catalyst. Oxygen absorbers are contemplated to be in any size or shape including sachet, pouch, canister, lining, sticker, etc. as well as part of the secondary packaging or primary packaging container itself.

EXAMPLES

The following examples are offered to illustrate but not to limit the invention.

Although the invention has been illustrated by the following examples, it is not to be construed as being limited thereby; but rather, the invention encompasses the generic area as hereinbefore disclosed. Various modifications and embodiments can be made without departing from the spirit and scope thereof.

Examples 1-2: Procedure of Subcutaneous Injection of 3 mg Sumatriptan

The procedure used for subcutaneous injection of 3 mg sumatriptan is: 1) Dissolve sodium chloride in 80 percent of water for injection required for the batch; 2) Add sumatriptan succinate to solution of step (1) and make the volume with remaining 20 percent of water for injection; 3) Mix the solution of step (2) till all the contents are dissolved; and Filter sterilize the solution of step (3) and dispense in suitable container/vial.

TABLE 1

Ingredients of the compositions of Examples 1 & 2

| Ingredients | Example 1 Quantity per Unit(%) | Example 2 Quantity per Unit(%) |
|---|---|---|
| Sumatriptan Succinate USP | 0.84 | 0.84 |
| Sodium Chloride USP | 0.83 | 0.84 |
| Water For Injection USP | QS to 100 | QS to 100 |
| Osmolality (mOsmol/Kg) | 288 | 293 |
| pH | 4.62 | 4.5 |

Example 3: Assessment of the Stability of the Composition of Example I

The stability of the composition of example 1 was assessed at two different conditions: A) 40° C. and 75% RH for 3 months; and B) 30° C. and 65% RH for 12 months. The results are shown in Table 2 below. The period of time after which the composition was assessed is indicated in each table.

TABLE 2

Stability data of the composition of Example 1

| Stability Condition | Appearance | pH | Color of solution (AU) | Impurity |
|---|---|---|---|---|
| 3 months 40° C. and 75% RH | Clear; colorless; solution; free from visible particulate matter | 4.7 | 0.005 | Impurity C = 0.10 Impurity 1 = 0.41 Impurity 3 = 0.44 |
| 12 months 30° C. and 65% RH | Clear; colorless; solution; free from visible particulate matter | 4.6 | 0.003 | Impurity C = 0.08 Impurity 1 = 0.48 Impurity 3 = 0.21 |

AU: Absorption units measured at 575 nm

Example 4: Assessment of Pharmacokinetics of Subcutaneous Sumatriptan Composition of Example I A single-center study in 36 healthy subjects to assess pharmacokinetics of subcutaneous sumatriptan composition of Example 1 was performed. The objective of this study was to characterize the PK profile of subcutaneous sumatriptan composition. The results are shown in Table 3 below.

TABLE 3

Summary of Pharmacokinetic parameters following a single SC injection of Example 1 and IMITREX ® 3 mg (0.25 ml from 0.5 ml of 6 mg injection)

| Pharmacokinetic Parameters | Mean ± SD | |
|---|---|---|
| | Example 1 | IMITREX ® 3 mg (0.25 ml from 0.5 ml of 6 mg injection) |
| $C_{max}$ (ng/mL) | 49.2 ± 9.85 | 45.6 ± 8.97 |
| $t_{max}$ (hr)$^a$ | 0.187 (0.0833, 0.350) | 0.248 (0.0828, 0.349) |
| $AUC_{o-t}$ (ng*hr/mL) | 57.5 ± 8.06 | 53.7 ± 7.26 |
| $AUC_{0-inf}$ (ng*hr/mL) | 59.4 ± 7.86 | 55.6 ± 7.42 |
| $AUC_{0-2}$ (ng*hr/mL) | 42.5 ± 6.35 | 39.5 ± 5.60 |
| t½ (hr) | 1.70 ± 0.358 | 1.67 ± 0.311 |

$^a t_{max}$ is presented as median (minimum, maximum)

Example 4: The Effect of Age, BMI, and Race on Plasma Concentrations of Subcutaneous Sumatriptan: A Pooled Analysis Oral, intranasal (IN), and subcutaneous (SC) injectable formulations of sumatriptan are approved by the Food and Drug Administration (FDA) and are marketed in the United States. SC sumatriptan has a better efficacy profile than oral and IN sumatriptan products. Absorption is more rapid with SC administration (time to reach maximum observed [peak] plasma concentration [$T_{max}$] for SC Imitrex® is 12 minutes (5-20 minutes), significantly shorter than that for the oral (2 to 2.5 hours) and nasal routes (60-90 minutes). As a result, onset of action with SC sumatriptan (10 minutes) is faster than with IN (30 to 45 minutes) or oral (45 to 60 minutes) delivery.

There are several published pharmacokinetic (PK) studies for sumatriptan; however, very few of these examine whether sumatriptan's PK metrics (i.e., $C_{max}$ [maximum plasma concentration], AUC [area under the plasma concentration vs. time curve]) are affected by covariates such as age, BMI, or race. In addition, sample size for many of these studies is small.

Currently SC sumatriptan is available in the U.S. in 4 and 6 mg dosage forms (Imitrex® STATdose, 0.5 ml) injections and as an injectable solution (Imitrex® injection, 3 mg/0.25 ml). The composition of Example 1 has been made for SC injection in a single-dose, 0.5-mL prefilled syringe as a ready-to-use disposable autoinjector. Two clinical pharmacology studies were conducted to support the PK bridge between Example 1 and Imitrex®. The efficacy profile of Example 1 is expected to be the same as existing 3-mg sumatriptan injection products (half of the 6 mg Imitrex® dosage form). Data were pooled from two pharmacology studies for sumatriptan PK metrics by age, BMI, and race for Example 1 and several Imitrex® products. Data from the two PK studies were pooled as the target populations and study methodologies were similar. The objective of this post hoc analysis, to analyze the effect of covariates on systemic exposure of sumatriptan, may provide insights into treatment outcomes.

Methods

The protocol was approved by the Chesapeake Research Review, Inc.

Institutional Review Board and the study was conducted in compliance with good clinical practice at Celerion Research (Tempe, A Z and Lincoln, Nebr.). All studies used a single-dose, open-label, randomized crossover design to determine relative bioavailability following SC administration of sumatriptan succinate in healthy fasted adults. Each study included Example 1 (3 mg/0.5 mL) vs. either Imitrex® injection (3 mg/0.25 ml or 6 mg/0.5 ml) or Imitrex® STATdose system (4 mg/0.5 ml or 6 mg/0.5 ml). Brief descriptions of the three studies follow.

Study 002 (CD-002): This 3-way crossover study compared Example 1 to Imitrex® injection 3 mg and 6 mg. Subjects were randomized to one of the six treatment sequences.

Study 003 (CD-003): This 3-way crossover study compared Example 1 to Imitrex® 4 mg STATdose system and 6 mg STATdose system. Subjects were randomized to one of the six treatment sequences.

All Studies: In each period, a single dose was administered SC over approximately 5 seconds. Pharmacokinetic samples were obtained pre-dose and at 0.083, 0.167, 0.25, 0.333, 0.5, 1, 1.5, 2, 3, 4, 6, 8, 10, and 12 hours post-dose. Subjects were confined from 8 hours before the first dose through the last sample after the final dose. Doses were separated by at least 2 days.

Plasma concentrations (Cp) of sumatriptan were determined usmg techniques known in the art. Pharmacokinetic parameters for each dosing session were determined using non-compartmental methods with WinNonlin Version 6.3 (Certara, Cary, N.C.) or SAS Version 9.3 (SAS Institute, Cary, N.C.). The following parameters were determined:

1. $C_{max}$: The maximum measured Cp, determined by examination of the data.

2. $AUC_{0-2}$: Area under the Cp vs. time curve from the time of drug administration to the 2-hour sample.

3. $AUC_{0-inf}$: Area under the concentration-time curve from the time of drug administration extrapolated to infinity. $AUC_{0-inf}$ is calculated as the sum of $AUC_{0-t}$ (where t is last measured non-zero concentration) plus the ratio of the last measurable Cp to the elimination rate constant. AUC was calculated by the linear trapezoidal method.

Graphics were prepared to examine the relationship between each of $AUC_{0-2}$, $AUC_{0-inf}$, and $C_{max}$ and the following covariates: weight (kg), BMI (kg/m$^2$), age (years), gender, and race (categorized as white, black, or other [two subjects, listed as "multiple" race were characterized as 'other']). For continuous covariates, the relationship between each metric and covariate was evaluated by linear regression (P and r values displayed) and a smoother (Supersmoother®). In addition, the value for each covariate was identified and the value for the metric for subjects below and above that covariate value was determined; the ratio of these values is reported. For categorical covariates, the mean for each group was identified; groups were compared by t test. Ratio of values for female/males and non-white I white were determined.

Results

Subject Disposition. Demographics characteristics are summarized in Table 4. All subjects were healthy and none used tobacco. The total number of sessions was 96 for Example 1, 35 for Imitrex injection 3 mg; 36 for Imitrex® STATdose 4 mg, and 68 for Imitrex® STATdose 6 mg.

TABLE 4

Demographic characteristics of the subjects in the three studies. Values for gender are counts; for the other metrics, values are mean (range).

| Metric | Study 001 (N = 26) | Study 002 (N = 36) | Study 003 (N = 36) |
|---|---|---|---|
| Gender | | | |
| Male | 13 | 17 | 16 |
| Female | 13 | 19 | 20 |
| Age (years) | 29.1 (21-45) | 31.7 (18-45) | 32.0 (18-45) |
| Weight (kg) | 78.3 (47.7-113.2) | 73.4 (49.3-109.6) | 74.8 (51.3-116.5) |
| Height (cm) | 169.9 (151-193) | 166.5 (151-184) | 166.7 (153-188) |
| BMI (kg/m2) | 27.0 (19.2-34.8) | 26.4 (19.6-34.6) | 26.7 (19.8-33.8) |

Effect of BMI: For most treatment groups, increasing BMI was associated with decreasing exposure for all three metrics (P<0.05 [linear regression] for each treatment group within each metric); exceptions were $AUC_{0-inf}$ for Imitrex, 3 mg (P=0.052) and $C_{max}$ for Imitrex® 4 mg (P=0.061). $AUC_{0-2}$ for stockier subjects (BMI >26.33) was 0.89-0.97 times the value for leaner subjects (BMI <26.33). For leaner subjects receiving Example 1, $AUC_0$-2 was slightly less than that for stockier subjects receiving 4 mg Imitrex® and larger than that for stockier subjects receiving 3 mg Imitrex®. $AUC_{0-inf}$ for stockier subjects was 0.87-0.97 times the value for leaner subjects. For leaner subjects receiving Example 1, $AUC_{0-inf}$ was less than that for stockier subjects receiving 4 mg Imitrex® and larger than that for stockier subjects receiving 3 mg Imitrex®. $C_{max}$ for stockier subjects was 0.88-0.98 times the value for leaner subjects. For leaner subjects receiving Example 1, $C_{max}$ was less than that for stockier subjects receiving 4 mg Imitrex® and larger than that for stockier subjects receiving 3 mg Imitrex®.

TABLE 5

Effect of BMI on systemic exposure to sumatriptan. Values are for subjects with BMI <26.33/for subjects with BMI ≥26.33.

| | Example 1 3 mg | Imitrex 3 mg (0.25 ml of 6 mg injection) | Imitrex 4 mg (STATdose) | Imitrex 6 mg (STATdose) |
|---|---|---|---|---|
| $AUC_{0-2}$ (ng/ml · hours) | 43.35/40.03* | 39.2/37.99* | 52.51/48.61* | 80.14/71.38* |

TABLE 5-continued

Effect of BMI on systemic exposure to sumatriptan. Values are for subjects with BMI <26.33/for subjects with BMI ≥26.33.

|  | Example 1 3 mg | Imitrex 3 mg (0.25 ml of 6 mg injection) | Imitrex 4 mg (STATdose) | Imitrex 6 mg (STATdose) |
|---|---|---|---|---|
| $AUC_{0-inf}$ (ng/ml · hours) | 62.41/54.76* | 57.23/52.46 | 72.24/70.94* | 112.22 103.22* |
| $C_{max}$ (ng/ml) | 51.2/45.2* | 48.1/43.65* | 59.45/57.90 | 90.5/78.40* |

*Lean and stocky subjects differ (P < 0.05) by t test.

Effect of Race: For Example 1, $AUC_{0-2}$ and $AUC_{0-inf}$ were lower in non-whites compared to whites; the ratio of medians was 0.84 and 0.89, respectively (Table 6).

TABLE 6

Effect of race on systemic exposure to sumatriptan. Values are ratio of the medians for non-whites/whites.

|  | Example 1 3 mg | Imitrex 3 mg (0.25 ml of 6 mg injection) | Imitrex 4 mg (STATdose) | Imitrex 6 mg (STATdose) |
|---|---|---|---|---|
| $AUC_{0-2}$ (ng/ml · hours) | 0.84* | 0.87 | 0.89 | 0.84 |
| $AUC_{0-inf}$ (ng/ml · hours) | 0.89* | 0.92 | 0.87 | 0.89 |
| $AUC_{0-inf}$ (ng/ml) | 0.82 | 0.89 | 0.89 | 0.82 |

*White subjects differ (P < 0.05) from non-white subjects by t test.

Safety. In 98 subjects exposed to SC sumatriptan, all reported AEs were among those currently described for marketed sumatriptan products. There were no deaths or related SAEs. Subjects were monitored for injection site reactions including pain, tenderness erythema/redness, and induration/swelling before dosing and at 6 and 12 hours after study drug administration in all periods. The incidence of injection site pain was 14%, lower than that observed with the Imitrex® injection 3 mg and 4 mg and 6 mg Imitrex® STATdose devices (39%, 42% and 53%, respectively). All these effects were mild in nature and resolved without medical intervention.

DISCUSSION

These post hoc exploratory analyses demonstrate a statistically significant impact of body size, assessed by BMI, on systemic exposure to sumatriptan administered as Example 1 or Imitrex®. For each treatment group, subjects with lower BMI had higher systemic exposure compared to subjects with higher BMI.

For BMI, the value of the BMI was used to divide subjects into two groups; then the value for each metric was compared between these groups. If the ratio were markedly less than unity, it would suggest that subjects with higher BMI experienced lower exposure for that metric. In turn, it might imply different dosing requirements as a function of that metric. For $C_{max}$ and $AUC_{0-2}$ (the two metrics that are probably most relevant to sumatriptan's efficacy), these ratio values for weight and BMI were>0.75 for all products.

These post hoc analyses demonstrate that sumatriptan exposure was lower in stockier subjects.

Subjects with a high BMI have an increased risk of cutaneous allodynia, a risk factor for chronic migraine. Patients with cutaneous allodynia respond poorly or suboptimally to triptans for treatment of episodic migraine. Therefore BMI may impact efficacy of sumatriptan or other triptans for episodic migraneurs.

In at least some of the previously described embodiments, one or more elements used in an embodiment can interchangeably be used in another embodiment unless such a replacement is not technically feasible. It will be appreciated by those skilled in the art that various other omissions, additions and modifications may be made to the methods and structures described above without departing from the scope of the claimed subject matter. All such modifications and changes are intended to fall within the scope of the subject matter, as defined by the appended claims.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one of skill in the art, for any and all purposes, such as in terms of providing a written description, all ranges disclosed herein also encompass any and all possible sub-ranges and combinations of sub-ranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into sub-ranges as discussed above. Finally, as will be understood by one skilled in the art, a range includes each individual member. Thus, for example, a group having 1-3 articles refers to groups having 1, 2, or 3 articles. Similarly, a group having 1-5 articles refers to groups having 1, 2, 3, 4, or 5 articles, and so forth.

What is claimed is:

1. A pre-filled autoinjector for treating acute migraine in a patient by subcutaneous administration, the autoinjector comprising:
    an aqueous solution comprising 4.2 mg sumatriptan succinate and sodium chloride in a range of 4.15 mg to 4.2 mg in a total volume of 0.5 mL;
    wherein the aqueous solution has osmolality between 275 to 315 mOsm/kg; and
    wherein administration of the aqueous solution results in a systemic exposure in the patient characterized by at least one of the following plasma profiles:
    $C_{max}$ of about 35 ng/mL to about 57 ng/mL;
    $AUC_{0-2}$ of about 30 ng·hr/mL to about 50 ng·hr/mL; and
    $AUC_{0-inf}$ of about 43 ng·hr/mL to about 70 ng·hr/mL.

2. The pre-filled autoinjector of claim 1 further comprising a pre-filled syringe disposed within the autoinjector, wherein the aqueous solution is housed within the pre-filled syringe.

3. The pre-filled autoinjector of claim 2, wherein the syringe contains 0.5 mL of the aqueous solution.

4. The pre-filled autoinjector of claim 2, wherein the syringe comprises a permeable part for sterilization with ethylene oxide.

5. The pre-filled autoinjector of claim 1, wherein the autoinjector is a single-use, ready-to-use, disposable autoinjector.

6. The pre-filled autoinjector of claim 1, wherein aqueous solution has a pH of about 4.2 to 5.3.

* * * * *